(12) United States Patent
Mena Benito et al.

(10) Patent No.: US 12,422,511 B2
(45) Date of Patent: Sep. 23, 2025

(54) FUNCTIONAL MAGNETIC RESONANCE IMAGING

(71) Applicant: KONINKLIJKE PHILIPS N.V., Eindhoven (NL)

(72) Inventors: Maria Estrella Mena Benito, Eindhoven (NL); Joanne Henriëtte Desirée Monique Westerink, Eindhoven (NL); Raymond Van Ee, Geldrop (NL); Timmy Robertus Maria Leufkens, Upplands Vasby (SE); Marieke Van Dooren, Arendonk (BE); Adrianus Johannes Maria Denissen, Moergestel (NL); Willem Huijbers, Tilburg (NL); Marco Matters, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 248 days.

(21) Appl. No.: 18/031,031

(22) PCT Filed: Oct. 15, 2021

(86) PCT No.: PCT/EP2021/078559
§ 371 (c)(1),
(2) Date: Apr. 10, 2023

(87) PCT Pub. No.: WO2022/084166
PCT Pub. Date: Apr. 28, 2022

(65) Prior Publication Data
US 2023/0375649 A1    Nov. 23, 2023

(30) Foreign Application Priority Data
Oct. 22, 2020    (EP) .................................. 20203355

(51) Int. Cl.
*G01R 33/48* (2006.01)
*A61B 5/00* (2006.01)
(Continued)

(52) U.S. Cl.
CPC .......... *G01R 33/4806* (2013.01); *A61B 5/055* (2013.01); *A61B 5/165* (2013.01);
(Continued)

(58) Field of Classification Search
CPC ............ G01R 33/4806; G01R 33/5608; G16H 30/40; G16H 10/20; A61B 5/055; A61B 5/165; A61B 5/4064; A61B 5/7296
See application file for complete search history.

(56) References Cited

U.S. PATENT DOCUMENTS 10,034,645 B1    7/2018 Williams
2009/0253982 A1*  10/2009 Wang ................... A61B 5/4884
                                                          600/419

(Continued)

FOREIGN PATENT DOCUMENTS

JP         202018537 A    10/2020

OTHER PUBLICATIONS

Kalcher, K., et al. "Rescale: Voxel-specific task-fMRI scaling using resting state fluctuation amplitude," NeuroImage. vol. 70, 2013. p. 80-88 (Year: 2013).*

(Continued)

*Primary Examiner* — Sean A Frith

(57) ABSTRACT

It is proposed to obtain information about a stress or anxiety level of a subject within a predetermined time period before, during and/or after a capture time of a fMRI scan image. Using this information, embodiments may provide additional/supplementary information that may aid, assist or otherwise improve interpretation of the fMRI scan image.

12 Claims, 4 Drawing Sheets

(51) Int. Cl.
*A61B 5/055* (2006.01)
*A61B 5/16* (2006.01)
*G01R 33/56* (2006.01)
*G16H 10/20* (2018.01)
*G16H 30/40* (2018.01)

(52) U.S. Cl.
CPC .......... *A61B 5/4064* (2013.01); *A61B 5/7296* (2013.01); *G01R 33/5608* (2013.01); *G16H 10/20* (2018.01); *G16H 30/40* (2018.01)

(56) References Cited

U.S. PATENT DOCUMENTS

2014/0288401 A1  9/2014  Ouwerkerk et al.
2017/0343634 A1* 11/2017  Lencz ................ G01R 33/4806

OTHER PUBLICATIONS

Soares, M., et al., "Stress Impact on Resting State Brain Networks," PLOS One. vol. 8(6), 2013. p. 1-9 (Year: 2013).*

Kalcher Klaudius et al: "Rescale: Voxel-specific task-fMRI scaling using resting state fluctuation amplitude", Neuroimage, Elsevier, Amsterdam, NL, vol. 70, Dec. 21, 2012 (Dec. 21, 2012), pp. 80-88.
Soares et al Stress Impact on Resting State Brain Networks, PLOS One vol. 8, No. 6, Jun. 19, 2013.
Archer et al "Functional Connectivity of Resting State, Working Memory and Inhibition Networks in Perceived Stress" Neurobiology of Stress, vol. 8, Feb. 1, 2018 p. 186-201.
Maron-Katz Adi et al "A Large Scale Perspective on Stress Induced Altercations in Resting State Networks" Scientific Reports, vol. 6, No. 1 Aug. 1, 2016.
International Search Report and Written Opinion From PC/EP2021/078559 Mailed Dec. 23, 2021.
Dr. jockers.com "14 Ways to Reduce Anxiety Naturally" Downloaded Apr. 4, 2023.
Silva et al "Challenges and Techniques for Presurgical Brain Mapping With Functional MRI" Neuroimage Clin 2018 17 p. 794-803.

* cited by examiner

FUNCTIONAL MAGNETIC RESONANCE IMAGING

CROSS REFERENCE TO RELATED APPLICATIONS

This application is a U.S. national phase application of International Application No. PCT/EP2021/078559 filed on Oct. 15, 2021, which claims the benefit of EP Application Serial No. 20203355.1 filed on Oct. 22, 2020 and is incorporated herein by reference.

FIELD OF THE INVENTION

The invention relates to Magnetic Resonance Imaging, and more particularly to supporting interpretation of Functional Magnetic Resonance Imaging (fMRI) scans

BACKGROUND OF THE INVENTION

Functional Magnetic Resonance Imaging (fMRI) is commonly used to study brain activity of a human subject. Analysis of fMRI scan images typically seeks to identify correlations between a subject's brain activation and a specific behavioural task (i.e. memory task) that is performed by the subject during the scan (i.e. at or during the capture time of MRI scan). fMRI scan analysis also aims to discover correlations with specific cognitive states, such as memory and recognition, induced in the subject.

Consequently, diagnosis and treatment of a subject can both be based on interpretation of information collected during an fMRI exploration.

SUMMARY OF THE INVENTION

The invention is defined by the claims.

According to examples in accordance with an aspect of the invention, there is provided a method for obtaining information for supporting interpretation of a functional Magnetic Resonance Imaging, fMRI, scan image of a region of a subject's brain, the method comprising:
  obtaining subject data comprising information about a determined stress or anxiety level of a subject at an assessment time, the assessment time being within a predetermined time period before, during and/or after a capture time of the fMRI scan image; and
  modifying the fMRI scan image based on the subject data so as to generate a modified fMRI scan image, wherein modifying the fMRI scan image comprises modifying one or more values of brain activity of the fMRI scan image based on the determined stress or anxiety of the subject at the assessment time.

Proposed concepts thus aim to provide schemes, solutions, concepts, designs, methods and systems pertaining to aiding or supporting analysis and/or interpretation of fMRI scan images of a subject's brain. In particular, embodiments of the invention propose that neuroimaging results can be influenced by the psychological nature or state of the subject. In particular, it is proposed that a subject's stress or anxiety before, during or and/or after fMRI scanning can influence the measurements and thus potentially impact interpretation and/or diagnosis of mental disorders.

Currently, standard analysis of fMRI scans in undertaking without consideration of a context of the subject prior-to or during MRI scanning. For instance, subjects with a tendency toward claustrophobia are often anxious or can experience high levels of stress during a fMRI investigation. Also, subjects may feel anxious in a time period (of minutes hours or even days) leading up to a MRI scan. Alternatively, or additionally, some subjects can experience high levels of stress or anxiety just before starting a MRI scan, Further, a majority of subjects become anxious during a MRI scanning process.

Proposed concepts may be based on the realisation that fMRI scans of a subject can be affected by the stress or anxiety of the subject in a time period before, during and/or after the fMRI capture process. According to such a realization, it is proposed to obtain information about a stress or anxiety level of a subject within a predetermined time period before, during and/or after a capture time of the fMRI scan image. Using this information, embodiments may provide additional/supplementary information that may aid, assist or otherwise improve interpretation of the fMRI scan image (e.g. by enabling an understanding of the stress or anxiety of the subject which, in turn, enables data of the fMRI scan image to be corrected, modified, compensated and/or contextualised for more accurate analysis).

Embodiments seek to obtain information about the stress or anxiety of subject before, during and/or after a capture time of the fMRI scan image of the subject's brain. This information may then be employed to assist in the interpretation or analysis of the fMRI scan image. Embodiments may therefore be of particular use for supporting clinical decision making. Exemplary usage applications may for example, relate to assessing, diagnosing or predicting the onset, treatment (outcome) or development of medical conditions and/or medical procedures. Embodiments may thus be of particular use in relation to neurological disorder assessment or treatment for example.

In other words, embodiments propose to generate supplementary information for supporting interpretation of the fMRI scan image of a subject's brain based on the stress or anxiety level of the subject at an assessment time within a predetermined time period before, during and/or after a capture time of the fMRI scan image. The generated supplementary information may aid clinical decision making. Accordingly, embodiments may be used in relation to treatment selection so as support a medical professional when selecting treatment for a subject. Such embodiments may also support clinical planning Improved Clinical Decision Support (CDS) may therefore be provided by proposed concepts.

According to proposals, information about the stress or anxiety level of the MRI-scanned subject may be leveraged to support improved (e.g. more accurate) interpretation of fMRI scans of the subject.

By way of example, some embodiments propose a method or system to measure induced contextual stress to aid interpretation of fMRI brain scans, the method/system comprising: (i) fMRI scanning; (ii) a component for the assessment of a subject's stress level; and (iii) an analysis unit for interpretation of the fMRI brain scans based on the subject's stress level. Various approaches to assessing the subject's stress level may be employed, including approaches based on: cortisol measurements; activity of brain regions; and peripheral physiological parameters (like skin conductance and heart rate).

In particular, it is proposed to generate supplementary information by modifying the fMRI scan image based on the subject data so as to generate a modified fMRI scan image. In this way, embodiments may generate one or more compensated, corrected or contextualized fMRI scan images that support interpretation (e.g. by reducing or removing an influence of the subject's stress/anxiety or by indicating portions of a scan images that may be affected by the subject's stress/anxiety).

More specifically, generating supplementary information comprises modifying (e.g. increasing or decreasing) one or more values of brain activity of the fMRI scan image based on the determined measure of stress or anxiety of the subject at the assessment time. In this way, a fMRI scan image may be corrected or compensated in a manner which removes (e.g. reduces) changes in values caused by the subject's stress of anxiety. Embodiments may therefore provide more accurate fMRI scan images, thus supporting more accurate analysis/interpretation.

Various approaches to obtaining subject data may be employed by embodiments. Stress/anxiety may manifest itself in many different forms and this may vary across different subjects. Purely by way of example, it is known that stress involves significant responses in the amygdala, hippocampus, and inferior frontal gyms. Furthermore, adrenal grands are the major player in the body's stress response (as they respond to stress by secreting hormones like adrenaline, testosterone, aldosterone, cortisol, etc.). A generally accepted standard for stress measurement is to measure the level of the stress hormone cortisol. After a stressful event, the body cortisol concentration gradually builds up until it reaches a peak after around 20-30 minutes (as measured in saliva for example).

Accordingly, in an embodiment, obtaining subject data may comprise: obtaining cortisol data comprising a measure of the subject's cortisol level at the assessment time; and determining a measure of stress or anxiety of the subject at the assessment time based on the obtained cortisol data. In this way, embodiments may employ a generally accepted approach to determining a measure of stress or anxiety of the subject.

In some embodiments, obtaining subject data may comprise: obtaining brain activity data comprising a measure of the subject's brain activity at the capture time; and determining a measure of stress or anxiety of the subject at the assessment time based on the obtained brain activity data. For instance, a stress or anxiety level of the subject may be estimated via concurrent fMRI scanning. In this way, instant and/or continuous information about the stress or anxiety level of the subject may be obtained from fMRI scan. In doing so, it may be preferable to synchronize the stress/anxiety measures with one or more tasks being performed by the subject during the MRI scanning process. Purely by way of example, the timing of a task (e.g. stressor) may be identified from a concurrent increase in hypothalamus, amygdala and/or hypophysis activity or physiological activity.

Also, obtaining brain activity data may comprise analysing a second fMRI scan image of one or more regions of the subject's brain, the second fMRI scan image being captured at the capture time. The second fMRI scan image may be of a plurality of different regions, each of the plurality of different regions being sampled at a different spatial and/or temporal resolutions. Then, analysing the second fMRI scan image may comprise compensating for the different spatial and/or temporal resolutions. Accordingly, for scanning of multiple brain areas, embodiments may take into account that scanning per area/region may occur using different resolution and timing scales. For example, one brain area/region may be sampled more often and with higher spatial resolution. Embodiments may therefore be configured to compensate for this. Embodiments may also take account of inhomogeneous signal distortion across the brain, thus improving accuracy.

Stress/anxiety may also manifests in a subject's body via the Autonomous Nervous System. This system has two branches: the parasympathetic branch (the 'rest-and-digest' system) and the sympathetic branch (the 'fight-or-flight' system). Activity in the sympathetic system is considered an indication of stress. Well-known physiological parameters that change under the influence of stress include heart rate, heart rate variability, skin conductance, and respiration, and adrenaline secretion. Accordingly, in some embodiments, obtaining subject data may comprise: obtaining physiological data comprising a measure of one or more physiological parameters of the subject at the assessment time; and determining a measure of stress or anxiety of the subject at the assessment time based on the obtained physiological data. By way of example, the one or more physiological parameters of the subject may comprise at least one of: skin conductance; heart rate; respiration rate; adrenaline level; heart rate variability; skin temperature; and pupil dilation.

In some embodiments, obtaining subject data may comprise: obtaining questionnaire data comprising information about the subject's answers to questions relating to his/her stress or anxiety level at the assessment time; and determining a measure of stress or anxiety of the subject at the assessment time based on the obtained questionnaire data. Stress and anxiety levels may thus be evaluated by means of self-report information/questionnaires. For instance, digital questionnaires may be filled out at different times before and after a MRI scan, e.g. by means of a dedicated software application on a smartphone, tablet computer or portable computing device.

Modifying (150) the fMRI scan image may comprise: processing the fMRI scan image and the subject data with a machine learning algorithm to generate a prediction of how the stress or anxiety of the subject affeceted the fMRI scan image; and generating the supplementary information based on the generated prediction. Embodiments may therefore leverage machine learning and artificial intelligence concepts in order to provide improved (e.g. more accurate) information for supporting interpretation of the fMRI scan image.

According to examples in accordance with yet another aspect of the invention, there is provided a method for interpreting a fMRI scan image of a subject's brain, the method comprising: obtaining information for supporting interpretation of a fMRI scan image of a region of a subject's brain according to a proposed embodiment; obtaining the fMRI scan image, the fMRI scan image being captured at a capture time; and interpreting the obtained fMRI scan image based on the obtained information.

According to examples in accordance with yet another aspect of the invention, there is provided a computer program product comprising computer program code means which, when executed on a computing device having a processing system, cause the processing system to perform all of the steps of the method described above.

According to examples in accordance with another aspect of the invention, there is provided a system for supporting interpretation of functional Magnetic Resonance Imaging, fMRI, scan image of a region of a subject's brain. The system comprises: an interface configured to obtain subject data comprising information about a determined stress or anxiety level of the subject at an assessment time, the assessment time being within a predetermined time period before, during and/or after a capture time of the fMRI scan image; and a processor arrangement configured to to modify the fMRI scan image based on the subject data so as to generate a modified fMRI scan image, wherein modifying the fMRI scan image comprises modifying one or more values of brain activity of the fMRI scan image based on the determined stress or anxiety of the subject at the assessment time.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
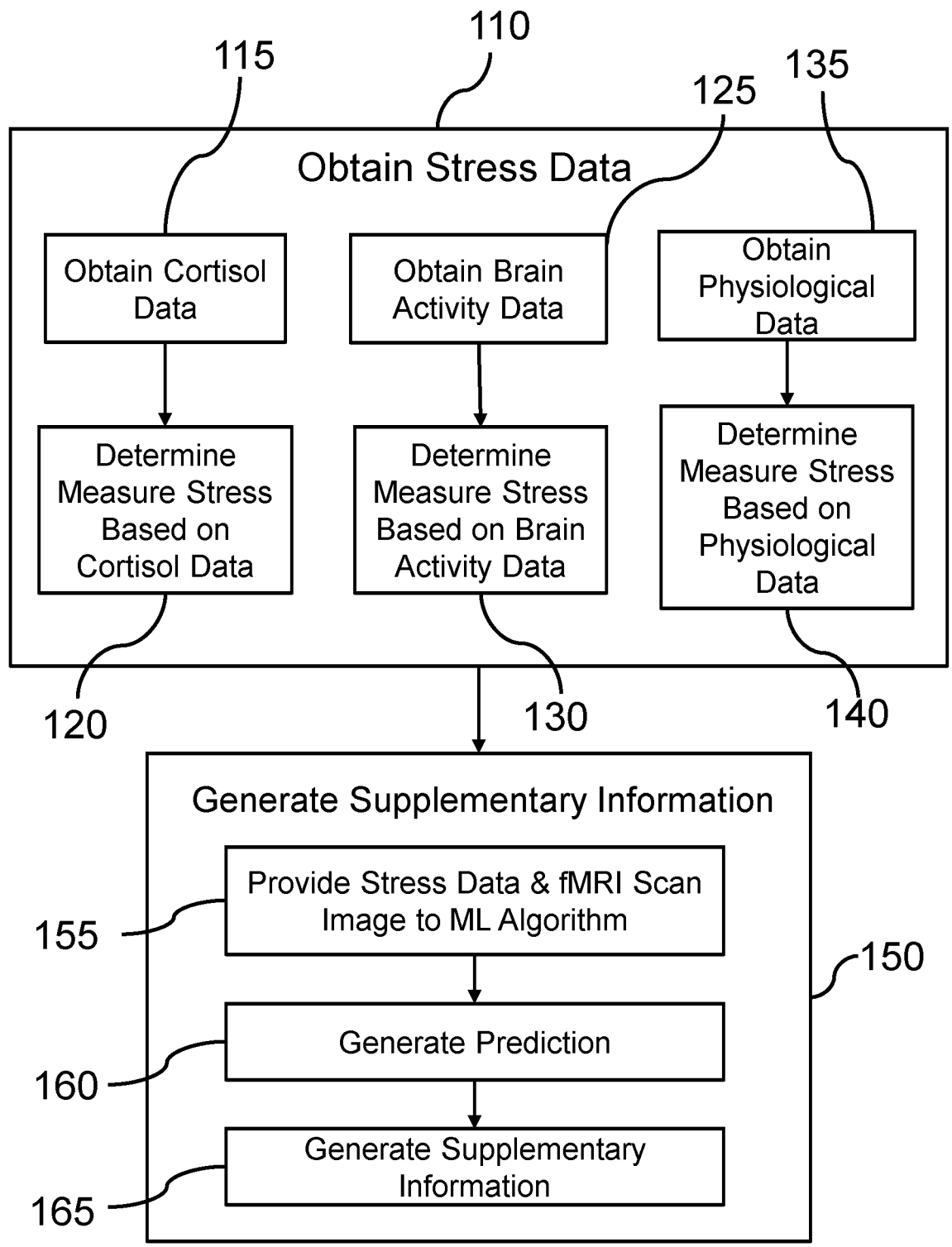
FIG. 1 depicts a flow diagram of a method for obtaining information for supporting interpretation of a fMRI scan image of a region of a subject's brain according to an exemplary embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The mere fact that certain measures are recited in mutually different dependent claims does not indicate that a combination of these measures cannot be used to advantage.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

It should be understood that the Figures are merely schematic and are not drawn to scale. It should also be understood that the same reference numerals are used throughout the Figures to indicate the same or similar parts.

Implementations in accordance with the present disclosure relate to various techniques, methods, schemes and/or solutions pertaining to aiding supporting analysis and/or interpretation of fMRI scan images of a subject's brain. According to proposed concepts, a number of possible solutions may be implemented separately or jointly. That is, although these possible solutions may be described below separately, two or more of these possible solutions may be implemented in one combination or another. In particular, proposed concepts may be based on the realisation that a subject's stress or anxiety before, during or and/or after fMRI scanning can influence a scan image. Leveraing this, embodiments are configured to determine a stress or anxiety level of a subject within a predetermined time period before, during and/or after a capture time of a fMRI scan image and then generate information that may aid interpretation of the fMRI scan image. Proposed embodiments may therefore provide an approach to generating and supplying useful information for fRMI scan analysis. Accordingly, embodiments may be used in relation to treatment selection and/or provide improved Clinical Decision Support (CDS).

Proposed embodiments may leverage known approaches to assessing a subject's stress or anxiety level. Results of such assessment may then be used to generate supplementary information that may aid, assist or otherwise improve interpretation of the fMRI scan image (e.g. by enabling an understanding of the stress or anxiety of the subject which, in turn, enables data of the fMRI scan image to be corrected, modified, compensated and/or contextualised for more accurate analysis). Such embodiments may, for example, be employed to diagnose, treat and/or predict neurological disorders.

FIG. 1 depicts a flow diagram of a method for obtaining information for supporting interpretation of a fMRI scan image of a region of a subject's brain according to an exemplary embodiment.

The method begins with step 110 of obtaining subject data. Specifically, the subject data comprises information about a determined stress or anxiety level of a subject at an assessment time. The assessment time is within a predetermined time period before, during and/or after a capture time of the fMRI scan image.

Different processes for undertaking the step 110 of obtaining subject data can be employed (individually or in combination). Purely by way of example, the embodiment of FIG. 1 comprises three separate methods/processes for obtaining subject data. One, two or all of the three methods/processes may be undertaken during the execution of step 110.

The first process comprises steps 115 and 120. In step 115 cortisol data comprising a measure of the subject's cortisol level at the assessment time is obtained (e.g. using a conventional method to measure a level of the stress hormone cortisol in the subject). Based on the obtained cortisol data, a measure of stress or anxiety of the subject at the assessment time based is determined in step 120.

The second process comprises steps 125 and 130. Step 125 comprises obtaining brain activity data which includes a measure of the subject's brain activity at the capture time of the fMRI scan image. Step 130 then comprises determining a measure of stress or anxiety of the subject at the assessment time based on the obtained brain activity data.

Purely by way of example, obtaining brain activity data may comprise analysing a second fMRI scan image of one or more regions of the subject's brain, the second fMRI scan image being captured at the capture time. If the second fMRI scan image is of a plurality of different regions, wherein each of the plurality of different regions is sampled at a different spatial and/or temporal resolutions, the step of analysing the second fMRI scan image can include compensating for the different spatial and/or temporal resolutions. This may account for situations where scanning per area/region uses different resolution and/or timing scales. For example, one brain area/region may be sampled more often and with higher spatial resolution, and this may be compensated for.

The third process comprises step 135 and 140. Step 135 comprises obtaining physiological data including a measure of one or more physiological parameters of the subject at the assessment time. For example, the one or more physiological parameters of the subject may comprise at least one of: skin conductance; heart rate; respiration rate; adrenaline level; heart rate variability; skin temperature; and pupil dilation. Step 140 then comprises determining a measure of stress or anxiety of the subject at the assessment time based on the obtained physiological data.

After step 110 of obtaining subject data has been completed, the method proceeds to step 130. Step 130 comprises generating supplementary information for supporting interpretation of the fMRI scan image based on the subject data. By way of example, in the embodiment of FIG. 1. Generating supplementary information comprises three sub-steps: 155; 160; and 165.

In step 155, the obtained subject data (from step 110) and the fMRI scan image is provided to a machine learning algorithm. The machine learning algorithm processes the subject data and the fMRI scan image in step 160 to generate a prediction (e.g. a prediction of how the stress/anxiety level of the subject altered/affected the fMRI scan image). Based on the generated prediction, supplementary information is generated in step 165. For instance, in step 165, the fMRI scan image is modified to generate a modified fMRI scan image. Such modification may, for example, comprises decreasing one or more values of the fMRI scan image based on the determined measure of stress or anxiety of the subject at the assessment time. In this way, a modified fMRI scan image may be generated which has its values corrected or adjusted to account for the stress of anxiety of the subject.

Although the embodiment of FIG. 1 has been described above as employing one or more of three different processes for obtaining information about a stress or anxiety level of a subject, it is to be understood that other processes may employed by proposed embodiments. For example, obtaining subject data may comprise obtaining questionnaire data including information about the subject's answers to questions relating to his/her stress or anxiety level at the assessment time. That is, information about a stress or anxiety of the subject may be provided to an embodiment by the subject.

Figure 2:
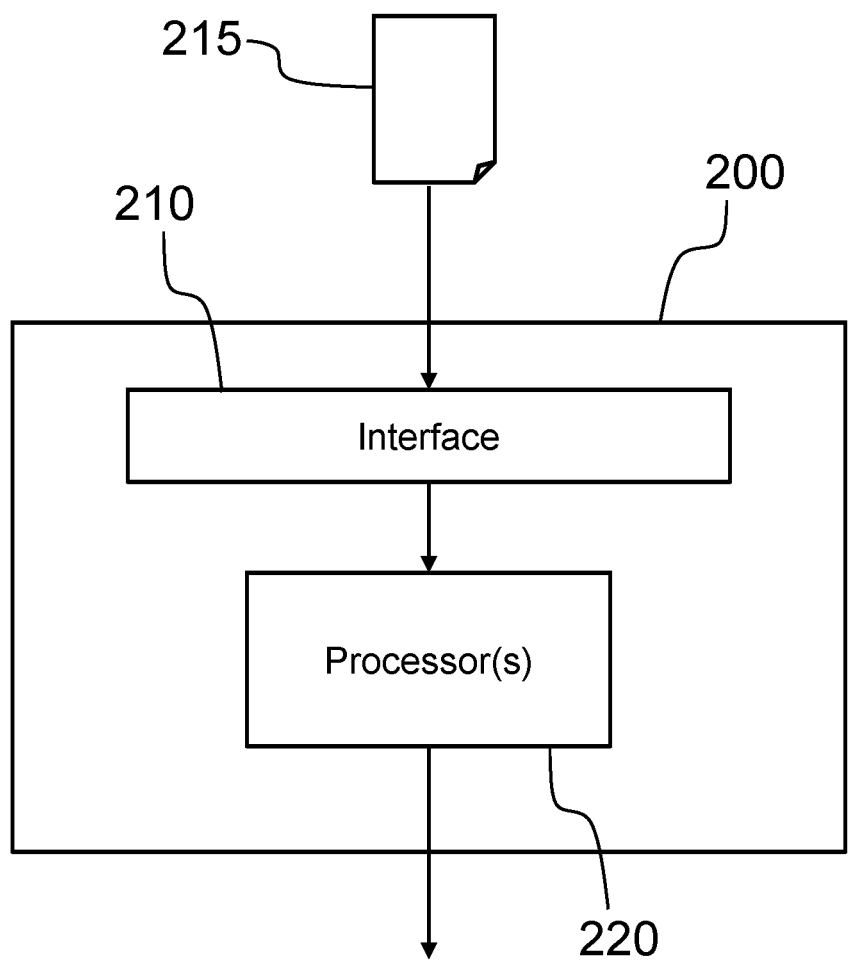
FIG. 2 depicts a simplified block diagram of a system 200 for supporting interpretation of a fMRI scan image of a region of a subject's brain according to an exemplary embodiment.

FIG. 2 depicts a simplified block diagram of a system 200 for supporting interpretation of a fMRI scan image of a region of a subject's brain according to an exemplary embodiment. The system 200 comprises an interface 210 (e.g. signal interface and/or user input interface configured to obtain subject data 215. The subject data comprises information about a determined stress or anxiety level of the subject at an assessment time (e.g. before, during and/or after a capture time of the fMRI scan image). The system 200 also comprises a processor arrangement 220 (of one or more micro-processors) that is configured to generate supplementary information for supporting interpretation of the fMRI scan image based on the subject data. The processors arrangement 220 is adapted to output the generated supplementary information, e.g. to a user, display device and/or another system.

Figure 3:
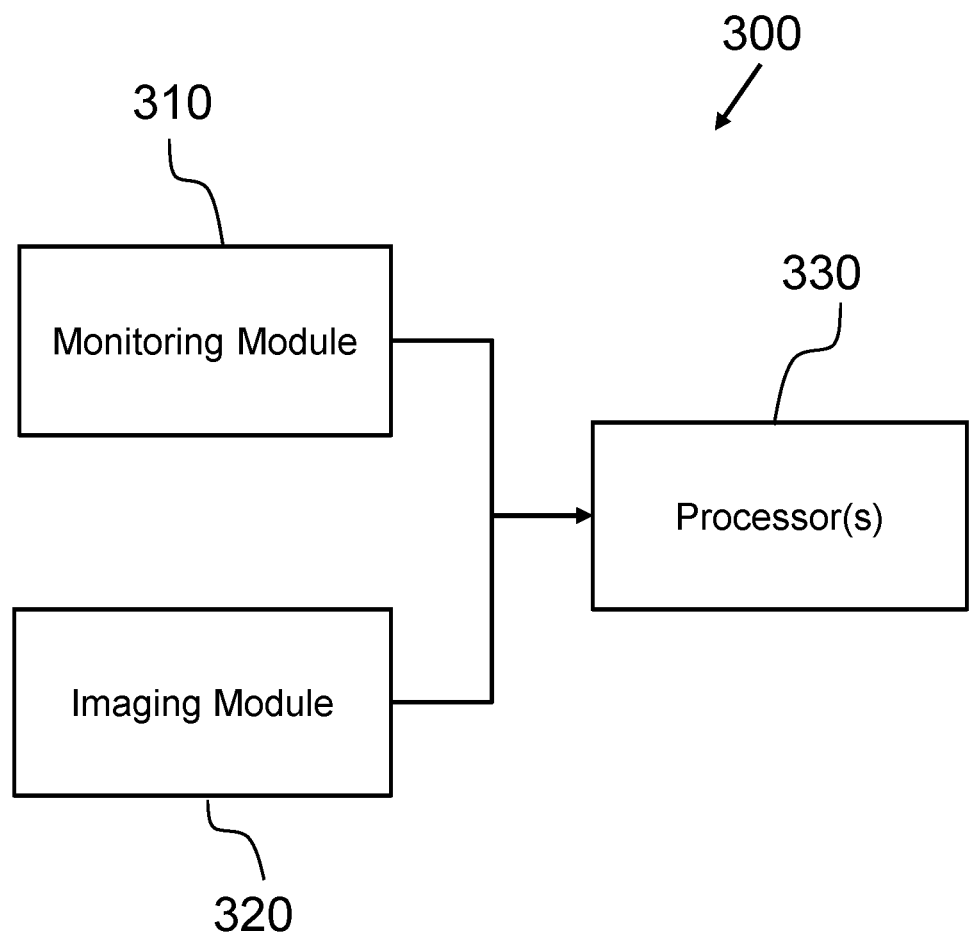
FIG. 3 is a simplified block diagram of a system according to another proposed embodiment.

FIG. 3 depicts a simplified block diagram of a system 300 according to another proposed embodiment. The system comprises a monitoring module 310, a fMRI imaging module 320, and a processor arrangement 330. Various aspects of the parts of the system 300 will now be described in the following respective sections.

Monitoring module 310—for assessment of patient stress level.

This module 310 is for measuring, monitoring and determination of the patient's stress and anxiety level. It is therefore configured to determine a stress and anxiety level based on measurement of objective parameters.

For instance, physiological signals can be measured by means of different approaches, and such signals may be collected in two different ways: single- or multiple-instant; or continuously A stress/anxiety level may be determined (at an assessment time) during the fMRI scan, and/or up to 24 hours prior and up to 24 hours after the fMRI scan. This may help to establish a more accurate stress baseline: i.e. lower stress levels may be found 24 hours before the scan.

Additionally, stress and anxiety levels can be evaluated by means of self-report information/questionnaires. For instance, digital questionnaires may be filled out at different moments before and after the scan, i.e. by means of a dedicated software application made available to the subject (e.g. via smartphone, tablet or portable computer).

Imaging module 320—for fMRI Imaging

The imaging module 320 is configured to measure and monitor brain activity during cognitive, perceptual or behavioural tasks. In order to use multiple brain areas for diagnosis, the module can account for the fact that scanned brain areas may have different resolution and timing scales. For example, one brain area could be sampled more often and with higher spatial resolution, and this may be accounted/compensated for. Inhomogeneous signal distortion across the brain may also be taken into account.

Processor Arrangement 330

For analysis of data from the monitoring module 310 and the imaging module 320, the processor arrangement 330 employs a reference library record of known one-to-one scientific learnings concerning specific brain areas that are related to specific forms of mental stress. Using such reference information, the processor arrangement can analyse the received data and determine a stress/anxiety level of the subject.

By way of demonstrating possible implementations of the system 300 of FIG. 3, various exemplary embodiments will now be detailed in the following sections.

Exemplary Embodiment 1: Patient's Stress Level Estimated on Cortisol Measurements The monitoring module 310 is configured for determination of cortisol level. By way of example, a cortisol level may be estimated as follows:

(i) via a hair sample that measures chronic (i.e. long-term) cortisol levels from the last months prior to the fMRI capture time. These can be used to determine a baseline or scalar values;

(ii) via single or multiple cortisol saliva swabs that measure acute levels of cortisol. Sampling might start in the morning, prior to the MRI scanning, to correct for fluctuations over the course of the day and continue during the examination;

(iii) via a continuously sampling blood line measuring plasma cortisol, preferably starting 30 minutes prior to scanning; or (iv) via indirect continuous sampling using physiological parameters, preferably starting 30 minutes prior to scanning.

The processor arrangement 330 is configured to synchronize various cortisol measures and correct for stress induced bias in fMRI measurements. Such correction for single- or multiple cortisol values could be done in the following way: The activity of the scanned images is (initially) decreased by 5% for each 1 nmol/L cortisol present. The figure of 5% can be adapted regularly on the basis of accumulated scans, in order to determine it more and more accurately. That is, although a standard value of 5% is detailed, it is only exemplary and other values may be employed, e.g. depending on the brain region of interest and/or the a particular neural network related to stress.

Thus, alternatively, correction for single- or multiple cortisol values could be done in a similar way: The activity of the scanned images is (initially) decreased with y % for each 1 nmol/L difference in the cortisol levels measured before the scan & during it. Again, the y % figure can be adapted regularly on the basis of accumulated scans, in order to determine it more accurately.

The correction using continuous cortisol measurement, can be undertaken similarly: The activity of the scanned images is (initially) decreased with z % for each 1 nmol/L cortisol present at least for a time window of 20-30 minutes before the MRI procedure was started. Thus, the images can be corrected for stress caused by the MRI scanner itself. Also, this figure of z % can be adapted regularly on the basis of accumulated scans, in order to determine it more and more accurately.

Alternatively, the continuous measurement could be used to create a delayed time-course for (slowly) changing cortisol measurement. This continuous cortisol time-series could be included a confound regressors during estimation of brain activity.

The long-term hair cortisol values can be used as a scalar to modify the level of brain activity. Alternatively, the long-term hair cortisol values could be used to scale the acute cortisol measures. For example, chronic stress can increase the galvanic skin conductance response to a stressor, or actually reduce the acute responses in saliva Several of these cortisol-based correction methods could be combined.

For example, for stress related to PTSD trauma, a relevant parameter is the volume and the relevant region of interest is the hippocampus (which is associated with placing memories in the correct context of space and time). For stress related to Major Depressive Disorder (MDD), the parameter would be the functional connectivity and the network of interest would be the default mode network.

Exemplary Embodiment 2: Patient's Stress Level Estimated on Peripheral Physiological Parameters (Like Skin Conductance) During Imaging Procedure Estimation of stress level is based on continuous information provided by peripheral physiological parameters like skin conductance or heart rate. Skin conductance and heart rate information can be collected by means of a wearable device, i.e. smart watch. Heart rate info can also be collected by means of a (PPG) camera. Such measurements involve reactions of the autonomous nervous system which is involved in the stress response.

In addition, skin conductance measurements can be processed (using known techniques) to estimate the amount of in-body cortisol, and as such provide an indication of stress approximately 20-30 minutes preceding. When the physiological measures are transformed into cortisol estimates by means of this technique, these cortisol estimates can be considered part of embodiment 1 above.

By way of further example, embodiments of the system 300 may employ an Artificial Intelligence (AI) module of Machine Learning algorithm (e.g. via the processor arrangement 330) for evaluation of stress level and interpretation of brain scans. The stress level estimates can be used as an absolute indicator of stress, signifying to what extent stress is expected to impact the brain images scanned. In addition, the stress levels can also be compared to those (directly) before the tasks were presented, thus separating the stressing effect of the scanning procedure from the stressing effects of the presented tasks. Either these relative or the absolute stress levels are then used to correct the brain scans in various ways, such as:

(a) Stress level (as measured in relation to a certain task) is used to correct estimates of task-evoked brain activity and employed to identify brain signals that are amplified or reduced under the influence of stress levels. It is known that brain activity level is different under stress, and we can use this information to correct the brain activity estimate. For continuous stress estimates, this could be done real-time.

(b) The correction for absolute stress levels can be done in the following way: The activity of the scanned images is (initially) decreased with x % for each unit of stress present. This figure of x % can be adapted regularly on the basis of accumulated scans, in order to determine it more and more accurately.

(c) The correction for relative stress values can be done in a similar way: The activity of the scanned images is (initially) decreased with y % for each unit difference in the stress levels measured before the scan & during it. Also here, the y % figure can be adapted regularly on the basis of accumulated scans, in order to determine it more accurately.

(d) The correction for scanning-protocol induced stress can be done similarly as well: The activity of the scanned images is (initially) decreased with z % for each unit of stress present just before the tasks were started. Thus, the images are corrected for the stressful impact of the scanner itself. Also this figure of z % can be adapted regularly on the basis of accumulated scans, in order to determine it more and more accurately.

The same method can be used to correct for stress differences between two (diagnostic) groups, while keeping the relative stress-related variance within a group similar.

Potential guidance for a clinical interpretation of the normalized brain measurement is then based on the corrected rather than the raw signal.

Embodiment 3—Patient's Stress Level Estimated from Measurements of Adrenal Gland Activity as Measured During the Same Imaging Procedure An indication of acute or subacute stress can be obtained from a fMRI scan of the adrenal gland (both cortex and medulla) activity. For wide enough and double bores, this adrenal gland activity can be measured during the same scan as the one that measures the brain activity. Estimation of stress level can be done by different approaches: (i) Adrenal activity values flag those images that were taken when adrenal activity levels were estimated to be high, indicating that the task was stressful for this individual, and that the outcome of the present task potentially is affected by stress; or (ii) Adrenal activity level (as measured in relation to a certain task) is used to augment/correct the intensity of the brain activity during that task. It is known that brain activity level is affected by stress, and this information can be used to correct/augment the brain activity estimate. This can be done in real-time.

Furthermore, a distinction is made between two areas of adrenal activity: when the medulla (kernel) of the adrenal gland is active, this indicates production of adrenaline, usually directly after the stressing event, and thus adrenal activity in the medulla is an indicator of acute stress (so similar corrections as in embodiments above are applicable). When the cortex of the adrenal gland is active, this indicates the production of cortisol, usually with some delay, and thus adrenal activity in the cortex is a measure of past stress (so similar corrections as in embodiment 1 above are applicable).

It will be understood from the description above, that there is proposed a approach for assisting and/or improving the interpretation of brain activity and consequently optimizing the neuroimaging interpretation. There are proposed method and systems for providing complementary information of a patient's stress level during fMRI examination. The information can, for example, be used for correcting the brain measurements itself, or for correcting the interpretation/analysis of the brain measurements.

Although various exemplary embodiments have been described, it will be understood that alternative embodiments and/or various modifications may be implemented. For instance, stress and anxiety levels can be evaluated by means of self-report information/questionnaires.

Additionally, stress information may be used to improve patient experience: reduction of the patient's stress level due to brain scanning, i.e. breathing exercises may be provided according to the subject's stress level, which may in turn improve the MRI scan process.

MRI investigation may include scans other than task-based fMRI scan. During these scans stress will be measured as well (which should be non-task induced stress).

In some embodiments, it is proposed to monitor twin subjects (i.e. twins). Such a proposal rests on the assumption that the brain activity in twins is similar. If one of the twins is claustrophobic, with associated brain activity, this activity can then be used to identify a claustrophobia-related brain area, for example.

Figure 4:
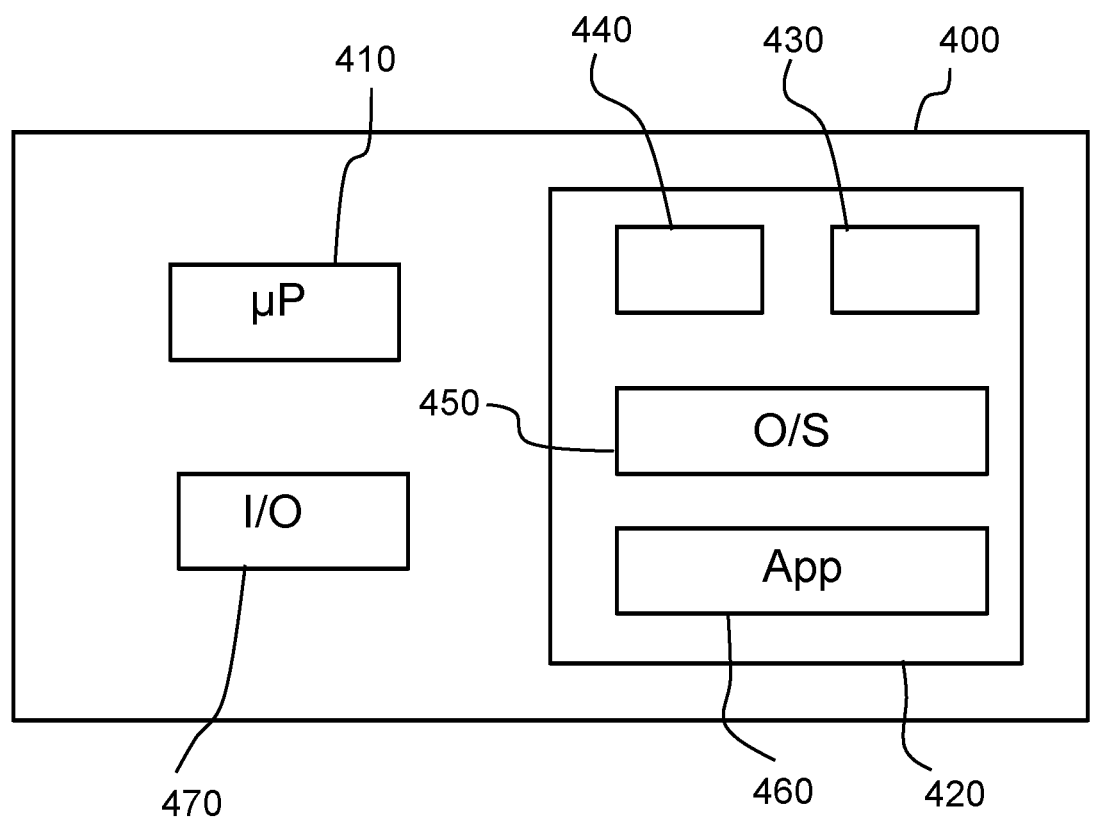
FIG. 4 illustrates an example of a computer within which one or more parts of an embodiment may be employed

By way of further example, FIG. 4 illustrates an example of a computer 400 within which one or more parts of an embodiment may be employed. Various operations discussed above may utilize the capabilities of the computer 400. For example, system for supporting interpretation of a fMRI scan image of a region of a subject's brain according may be incorporated in any element, module, application, and/or component discussed herein. In this regard, it is to be understood that system functional blocks can run on a single computer or may be distributed over several computers and locations (e.g. connected via internet).

The computer 400 includes, but is not limited to, PCs, workstations, laptops, PDAs, palm devices, servers, storages, and the like. Generally, in terms of hardware architecture, the computer 400 may include one or more processors 410, memory 420, and one or more I/O devices 470 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 410 is a hardware device for executing software that can be stored in the memory 420. The processor 410 can be virtually any custom made or commercially available processor, a central processing unit (CPU), a digital signal processor (DSP), or an auxiliary processor among several processors associated with the computer 400, and the processor 410 may be a semiconductor based microprocessor (in the form of a microchip) or a microprocessor.

The memory 420 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 420 may incorporate electronic, magnetic, optical, and/or other types of storage media. Note that the memory 420 can have a distributed architecture, where various components are situated remote from one another, but can be accessed by the processor 410.

The software in the memory 420 may include one or more separate programs, each of which comprises an ordered listing of executable instructions for implementing logical functions. The software in the memory 420 includes a suitable operating system (O/S) 450, compiler 440, source code 430, and one or more applications 460 in accordance with exemplary embodiments. As illustrated, the application 460 comprises numerous functional components for implementing the features and operations of the exemplary embodiments. The application 460 of the computer 400 may represent various applications, computational units, logic, functional units, processes, operations, virtual entities, and/or modules in accordance with exemplary embodiments, but the application 460 is not meant to be a limitation.

The operating system 450 controls the execution of other computer programs, and provides scheduling, input-output control, file and data management, memory management, and communication control and related services. It is contemplated by the inventors that the application 460 for implementing exemplary embodiments may be applicable on all commercially available operating systems.

Application 460 may be a source program, executable program (object code), script, or any other entity comprising a set of instructions to be performed. When a source program, then the program is usually translated via a compiler (such as the compiler 440), assembler, interpreter, or the like, which may or may not be included within the memory 420, so as to operate properly in connection with the O/S 450. Furthermore, the application 460 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 470 may include input devices such as, for example but not limited to, a mouse, keyboard, scanner, microphone, camera, etc. Furthermore, the I/O devices 470 may also include output devices, for example but not limited to a printer, display, etc. Finally, the I/O devices 470 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 470 also include components for communicating over various networks, such as the Internet or intranet.

If the computer 400 is a PC, workstation, intelligent device or the like, the software in the memory 420 may further include a basic input output system (BIOS) (omitted for simplicity). The BIOS is a set of essential software routines that initialize and test hardware at startup, start the O/S 450, and support the transfer of data among the hardware devices. The BIOS is stored in some type of read-only-memory, such as ROM, PROM, EPROM, EEPROM or the like, so that the BIOS can be executed when the computer 400 is activated.

When the computer 400 is in operation, the processor 410 is configured to execute software stored within the memory 420, to communicate data to and from the memory 420, and to generally control operations of the computer 400 pursuant to the software. The application 460 and the O/S 450 are read, in whole or in part, by the processor 410, perhaps buffered within the processor 410, and then executed.

When the application 460 is implemented in software it should be noted that the application 460 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 460 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

A single processor or other unit may fulfill the functions of several items recited in the claims.

It will be understood that the disclosed methods are computer-implemented methods. As such, there is also proposed a concept of a computer program comprising code means for implementing any described method when said program is run on a processing system.

The skilled person would be readily capable of developing a processor for carrying out any herein described method. Thus, each step of a flow chart may represent a different action performed by a processor, and may be performed by a respective module of the processing processor.

As discussed above, the system makes use of a processor to perform the data processing. The processor can be implemented in numerous ways, with software and/or hardware, to perform the various functions required. The processor typically employs one or more microprocessors that may be programmed using software (e.g. microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted that the term "adapted to" is intended to be equivalent to the term "configured to". Any reference signs in the claims should not be construed as limiting the scope.

The invention claimed is:

1. A computer-implemented method for generating a modified functional Magnetic Resonance Imaging (fMRI) scan image, the method comprising:
receiving, by one or more processors, a functional Magnetic Resonance Imaging (fMRI) scan image, wherein the fMRI scan image includes at least a portion of a subject's brain;
receiving, by the one or more processors, subject data including information about a determined stress or anxiety level of a subject at an assessment time, the assessment time being within a predetermined time period before, during and/or after a capture time of the fMRI scan image;

modifying, by the one or more processors, the fMRI scan image based on the subject data, wherein the modifying the fMRI scan image includes modifying one or more values of brain activity of the fMRI scan image based on the determined stress or anxiety of the subject at the assessment time; and generating, by the one or more processors, a modified fMRI scan image based on the modified one or more values of brain activity to support interpretation by removing or reducing the determined stress or anxiety from the fMRI scan image.

2. The computer-implemented method of claim 1, wherein receiving subject data comprises:

obtaining cortisol data comprising a measure or estimate of the subject's cortisol level at the assessment time; and determining a measure of stress or anxiety of the subject at the assessment time based on the obtained cortisol data.

3. The computer-implemented method of claim 1, wherein receiving subject data comprises:

obtaining brain activity data comprising a measure of the subject's brain activity at the assessment time; and determining a measure of stress or anxiety of the subject at the assessment time based on the obtained brain activity data.

4. The computer-implemented method of claim 3, wherein receiving brain activity data comprises:

analyzing a second fMRI scan image of one or more regions of the subject's brain, the second fMRI scan image being captured at the capture time.

5. The computer-implemented method of claim 4, wherein a second fMRI scan image is of a plurality of different regions, each of the plurality of different regions being sampled at a different spatial and/or temporal resolutions, and wherein analyzing the second fMRI scan image comprises compensating for the different spatial and/or temporal resolutions.

6. The computer-implemented method of claim 1, wherein receiving subject data comprises:

obtaining physiological data comprising a measure of one or more physiological parameters of the subject at the assessment time; and determining a measure of stress or anxiety of the subject at the assessment time based on the obtained physiological data.

7. The computer-implemented method of claim 6, wherein the one or more physiological parameters of the subject comprise at least one of: skin conductance; heart rate; respiration rate; adrenaline level; heart rate variability; skin temperature; or pupil dilation.

8. The computer-implemented method of claim 1 wherein receiving subject data comprises:

obtaining questionnaire data comprising information about the subject's answers to questions relating to his/her stress or anxiety level at the assessment time; and determining a measure of stress or anxiety of the subject at the assessment time based on the obtained questionnaire data.

9. The computer-implemented method of claim 1, wherein generating the modified fMRI scan image comprises:

processing the fMRI scan image and the subject data with a machine learning algorithm to generate a prediction of how the stress or anxiety of the subject affected the fMRI scan image; and modifying the fMRI scan image based on the generated prediction.

10. The computer-implemented method of claim 1, further including:

interpreting, by the computer, the modified fMRI scan image, wherein interpreting the modified fMRI scan image is based on a difference in time between the assessment time and the capture time.

11. A computer program product comprising computer program code stored on a non-transitory computer readable medium which, when executed on a computing device having a processing system, cause the processing system to perform the computer-implemented method of claim 1.

12. A system comprising:

an interface configured to obtain subject data comprising information about a determined stress or anxiety level of the subject at an assessment time, the assessment time being within a predetermined time period before, during and/or after a capture time of a functional Magnetic Resonance Imaging (fMRI) scan image; and a processor coupled to the interface, wherein the processor is configured to receive the fMRI scan image; configured to modify the fMRI scan image based on the subject data by modifying one or more values of brain activity of the fMRI scan image based on the determined stress or anxiety of the subject at the assessment time; and generate a modified fMRI scan image, based on the modified one or more values of brain activity to support interpretation by removing or reducing the determined stress or anxiety from the fMRI scan image.

* * * * *